Figure 1:
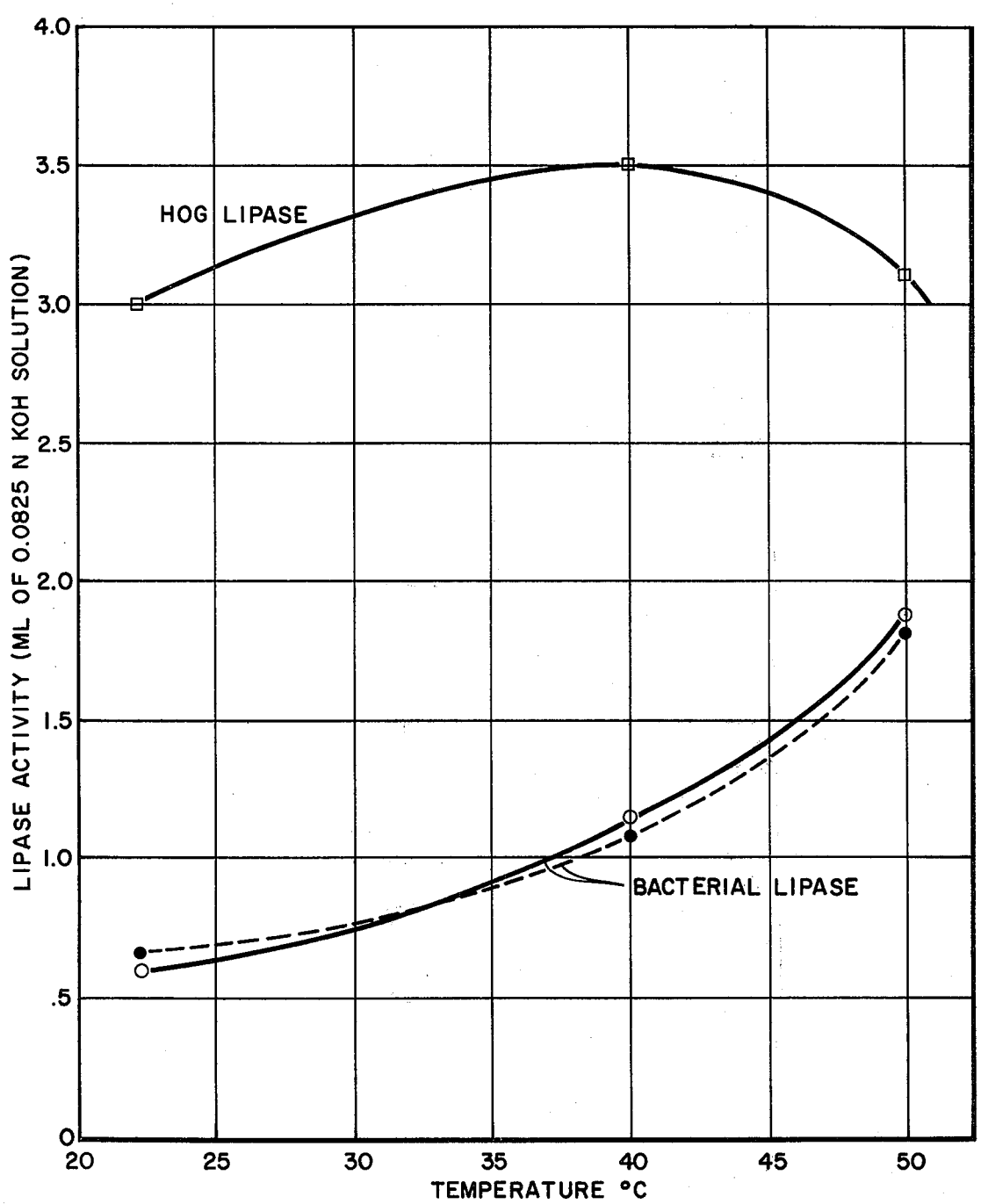

United States Patent [19]

Gawel et al.

[11] 4,019,959

[45] Apr. 26, 1977

[54] BACTERIAL PRODUCTION OF LIPASE AND PYOCYANINE FROM N-PARAFFINS

[75] Inventors: Len J. Gawel, Ponca City, Okla.; Chi-Sin Chen, San Jose, Calif.

[73] Assignee: Continental Oil Company, Ponca City, Okla.

[22] Filed: Oct. 6, 1975

[21] Appl. No.: 620,490

[52] U.S. Cl. .............................. 195/66 R; 195/65
[51] Int. Cl.$^2$ ................... C12D 13/10; C07G 7/02
[58] Field of Search .............. 195/62, 63, 65, 66 R, 195/80 R, 28 R

[56] References Cited

OTHER PUBLICATIONS

Merck Index, 8th Ed., p. 888.

*Primary Examiner*—Raymond N. Jones
*Assistant Examiner*—Robert J. Warden
*Attorney, Agent, or Firm*—Cortlan R. Schupbach, Jr.

[57] ABSTRACT

A method of producing lipase and pyocyanine from n-paraffins by growing a pseudomonas-like hydrocarbon oxidizing bacteria thereon and extracting the lipase and pyocyanine from the intracellular portion of the bacterium.

6 Claims, 3 Drawing Figures

BACTERIAL PRODUCTION OF LIPASE AND PYOCYANINE FROM N-PARAFFINS

The present invention relates to a method of producing lipase and pyocyanine. More specifically, the present invention relates to a method for producing lipase and pyocyanine by growing a pseudomonas-like hydrocarbon oxidizing bacterium on n-paraffins and extracting the lipase and pycocyanine from the interior of the bacteria cells.

Lipase is an enzymatic material that breaks down fats (lipids). These enzymes hydrolyze esters of glycercol and are sometimes referred to as glycerol-ester hydrolases. Lipases have many industrial uses. They find important applications in food quality control research and in the identification of microorganims. Presently, commercial lipase is obtained from mold, animal pancreas, or plant sources. The lipase enzyme is used industrially for various food processing steps such as chocolate hydrolysis and cheese production, for cleaning operations such as spot removal and drain cleaning, and has medicinal uses such as human and animal digestive aids. The enzyme is also used for the enzymatic hydrolysis of oil and fat for soap manufacturing and for the tanning of leathers and feedstuffs for animals. Pyocyanine is known to be effective as an antimicrobial agent.

Although many organisms are known to produce lipase, only recently was it found that the enzyme could be produced by mold or yeast cultures (Agricultural and Biological Chemistry, Volume 27, page 396, 1963).

Because hydrocarbons are considerably cheaper feedstock than conventional substrates that might be used for lipase production, the advantage of using a hydrocarbon oxidizer to produce lipase is self-evident. Lipase producing micororganisms can be easily cultivated in a controlled environment and can produce an enzyme product of uniform quality at relatively low cost. It is, therefore, desirable that such organisms and methods be developed.

It is therefore an object of the present invention to provide a process whereby a hydrocarbon oxidizing bacterial culture can be made to rapidly produce pyocyanine pigment and lipase using relatively inexpensive hydrocarbon substrates. Other objects will become apparent to those skilled in this art as the description proceeds.

It has now been discovered in accordance with the present invention that lipase can be produced by hydrocarbon oxidizing bacterial cultures in various media that contain substrates such as olive oil or n-paraffins. By rupturing the bacterial cells produced, the amount of intracellular lipase recovery can be significantly increased. Since the enzyme shows good stability in relatively adverse temperature and pH environments, it has good potential for application in industrial uses. Pyocyanine pigments are also obtained during the process of the present invention.

Although many hydrocarbon substrates can be utilized, substrates such as olive oil and the n-paraffins are preferred. Most preferred are the n-paraffins containing from 10 to 22 carbon atoms. Representative examples of such n-paraffin hydrocarbons are decane, undecane, dodecane, tetradecane, hexadecane, octadecane, nonedecane, eicosane, and docosane.

In the process of the present invention, the bacterium is allowed to grow on the substrate, preferably under optimum pH and temperature conditions, following which the bacteria are separated by filtering or centrifuging the bacterial cells away from the medium, rupturing the separated bacterial cells, and recovering the pyocyanine and lipase from the interior of the cells. The bacterial lipase of the present invention shows excellent activity at 50° C and good heat stability at 70° C. The lipase demonstrated an alkaline activity optimum, having very high activity at about pH 9. In the process of the present invention, the bacterium also produced a pyocyanine pigment which is known to possess antibacterial properties for gram negative organisms.

In the process of the present invention, the bacterial culture is allowed to grow on the substrate at a temperature of from 20 to 50° C for a period of time ranging from 10 to 100 hours. At the end of the growth cycle, the cells are isolated from the growth medium, the cell walls are ruptured using techniques known in the art, and the lipase and pyocyanine are isolated using techniques well known to those skilled in this art.

The bacterial culture of the present invention was originally isolated from an oil contaminated marine sediment environment exposed by low tide at Yaquina Bay, Newport, Oregon, United States of America, and tentatively identified as a pseudomonas species, the microorganism has been duly deposited with the United States Department of Agriculture and has been assigned strain designation NRRL B-8110. The culture, maintained on an agar slant of Tryptone Glucose Extract Agar (TGE), was transferred to 100 milliliters of liquid medium contained in a flask. The flask was incubated at 30° C on a gyratory shaker at 200 revolutions per minute. During a logarithmic growth phase, the entire culture was added to 1 liter of growth medium in a 2-liter flask which was then incubated under the same conditions.

Comparative testing of the bacteria of this invention with known bacteria strains was carried out. Known bacteria tested in the process of the initial invention failed to produce pyocyanine and lipase.

During large scale lipase production, a New Brunswick 14-liter fermenter equipped with a funnel-shaped draft tube was used (described in U.S. Pat. No. 3,660,244). The draft tube was used to disperse the oily substrate in the medium. An inoculum transfer consisting of 1 liter of the shake flask culture was added to the fermenter which contained 5 liters of medium. Agitation and aeration were maintained at 600 rpm and 0.2 volume per volume liquid per minute. The temperature was maintained at 30° and the pH controlled at 6.5 using $NH_4OH$.

Production of pyocyanine pigment was carried out during lipase production tests using both shake flask and fermenter methods described for lipase production.

The invention is more concretely described with reference to the examples below wherein all parts and percentages are by weight unless otherwise specified. The examples are intended to be descriptive and are not limiting on the present invention.

During the course of the experiments described below, the reagents used are as follows. Hog pancreatic lipase was a commercial lipase obtained from Pierce Chemical Company and was routinely employed as an active lipase control throughout the experiments. The standard alcoholic potassium hydroxide solution was prepared by dissolving 5.6 grams of potassium hydroxide pellets in 1 liter of 60 percent ethanol solution to give an approximately 0.1 N solution which was standardized against a standard .1000 N hydrochloric acid solution. The 0.067 M phosphate buffer having a pH of 8.2 was prepared by mixing approximately 4 parts of (A) solution with 9.6 parts of (B) solution until the pH reached 8.2. The (A) solution was 0.067 M $KH_2PO_4$, equaling 9.07 grams $KH_2PO_4$ per liter of distilled water. The (B) solution was 0.067 M $Na_2HPO_4$, equaling 11.88 grams $Na_2HPO_4 \cdot 2H_2O$ per liter of distilled water. The phenolphthalein solution was a 5 percent phenolphthalein solution in ethanol diluted with an equal volume of water and filtered. The tris-buffer was a 0.1 M solution used to substitute the 0.067 M phosphate buffer in studying the pH effect on lipase activity.

Table 1 shows the composition of TGE medium for maintaining culture. For measuring lipase production, a complex soybean dextrin (SDL) medium, a semicomplex grease splitting (GSM) medium, and four different mineral salts media (LM) were used. The compositions of these media are shown in Tables 2, 3, and 4. Stimulated pyocyanine pigment formation was accomplished by using bacto-peptone, neopeptone, protease peptone, or trypticase medium at 1 percent in water (Table 5). Compositions of n-paraffins used as lipase inducers in substrates are given in Table 6. These paraffins were primarily composed of $C^{12}$–$C^{14}$ n-paraffins with $C^{13}$ predominating. In addition to the n-paraffins, pale oil 170 containing predominantly cycloparaffin and a small quantity of n-paraffins were also investigated for lipase production. Olive oil was primarily used as a substrate for determining lipase activity. In preparing emulsified olive oil for the assay, polyvinyl alcohol (Dupont's Elvanol) of grades 72 through 60 was used.

Enzyme production by bacterial culture as a function of growth time was determined using whole cell assays after 3, 4, and 6 days of incubation, with the results shown in Table 7. LM-3 medium containing n-paraffin or pale oil 170 showed increased lipase activity with incubation time. When the culture was grown on complex SDL medium containing n-paraffin, very little lipase was found even after 20 days of incubation.

Enzyme production and semicomplex GSM medium containing olive oil or hydrocarbon was examined after 5 days of incubation. The results are shown in Table 8. Both olive oil and hydrocarbon induced the bacteria to produce intracellular as well as extracellular lipase in this medium. Regardless of substrate, more extracellular than intracellular lipase was found. Lipases produced from the hydrocarbon were approximately four times as active as those produced from the olive oil. A threefold increase in hydrocarbon-induced bacterial intracellular lipase activity was noted when the assay temperature was increased from 25° C to 50° C. In contrast, an opposite temperature effect was found for the hog lipase control.

TABLE 1

TRYPTONE GLUCOSE EXTRACT AGAR

| | |
|---|---|
| Bacto-Beef Extract | 3 grams |
| Bacto-Tryptone | 5 grams |
| Bacto-Dextrose | 1 gram |
| Bacto-Agar | 15 grams |

TABLE 2

SOYBEAN DEXTRIN LIQUID MEDIUM (SDL MEDIUM)

| | |
|---|---|
| Ground Soybean Meal | 30 grams |
| Dextrin | 5 grams |
| $K_2HPO_4$ | 5 grams |
| $(NH_4)_2SO_4$ | 1 gram |
| Distilled Water | 1 liter |
| n-Paraffin or Olive Oil | 15 grams |

TABLE 3

GREASE SPLITTING MEDIUM (GSM MEDIUM)

| | |
|---|---|
| Bacto-Nutrient Broth | 8 grams |
| Synthetic Sea Salt | 0.2 gram |
| Aspartic Acid | 0.5 gram |
| $K_2HPO_4$ | 1 gram |
| Distilled Water | 1 liter |
| pH | 6.8 |
| n-Paraffin or Olive Oil | 15 grams |

TABLE 4

MINERAL SALTS MEDIA (LM MEDIUM)

| | CONCENTRATIONS IN GRAMS PER LITER DISTILLED WATER | | | |
|---|---|---|---|---|
| | LM-1 | LM-2 | LM-3 | LM-4 |
| $(NH_4)_2SO_4$ | 3 | 3 | 5 | 5 |
| $K_2HPO_4$ | 5 | 3 | 3 | 3 |
| $ZnSO_4 \cdot 7H_2O$ | 0.005 | 0.005 | 0.005 | 0.005 |
| $MgSO_4 \cdot 7H_2O$ | 1 | 1 | 0.5 | 0.5 |
| $FeCl_3 \cdot 6H_2O$ | 0.01 | 0.01 | 0.01 | 0.01 |
| $CaCl_2$ | 0.01 | 0.01 | 0.01 | 0.01 |
| Yeast Extract | 1 | 0.2 | 0.2 | 0.2 |
| Aspartic Acid | — | — | — | 0.5 |
| pH | 7.2 | 7.0 | 7.0 | 7.0 |
| n-Paraffin or Olive Oil | 15 | 15 | 15 | 15 |

TABLE 5

PEPTONE MEDIUM (P MEDIUM)

| | |
|---|---|
| Bacto-Peptone[1] | 10 grams |
| Distilled Water | 1 liter |
| n-Paraffin or Olive Oil | 15 grams |

[1]Neopeptone, Protease Peptone, or Trypticase

TABLE 6

COMPOSITION OF n-PARAFFIN SUBSTRATE

| Alkane | Wt. Percent | Alkane | Wt. Percent |
|---|---|---|---|
| $C_{10}$ | 0 | $C_{14}$ | 39 |
| $C_{11}$ | 0 | $C_{15}$ | 0.2 |
| $C_{12}$ | 11 | $C_{16}$ | 0 |
| $C_{13}$ | 49 | $<C_{16}$ | 0 |
| Total n-paraffin = 97.0 | | | |
| Aromatic = 0.2 | | | |
| Branched paraffin = 2.8 | | | |
| (Avg. Molecular Weight = 185) | | | |

TABLE 7

WHOLE CELL BACTERIAL LIPASE ACTIVITIES AT VARIOUS CULTURE AGES

| | | LIPASE ACTIVITES AT 22° C | | | |
|---|---|---|---|---|---|
| Medium | Lipase Inducer | 3 Days | 4 Days | 6 Days | 20 Days |
| LM-3 | n-Paraffin | 1.4 | 1.9 | 1.85 | — |
| | Pale Oil 170 | 1.6 | 2.2 | 2.5 | — |
| SDL | n-Paraffin | — | 0.0 | — | 0.1 |

TABLE 8

BACTERIAL LIPASE ACTIVITIES - GSM SHAKE FLASK GROWTH

| Lipase Inducer | Enzyme Preparation | LIPASE ACTIVITY at 22° C | at 50° C |
|---|---|---|---|
| Olive Oil | Intracellular | 0.13 | — |
|  | Extracellular | 0.25 | — |
| n-Paraffin | Intracellular | 0.67 | 1.95 |
|  | Extracellular | 0.80 | — |
|  | Hog Lipase | 3.10 | 2.31 |

Bacterial lipase was grown in LM-1 medium, and lipase activities of the intracellular and extracellular preparations were prepared, with the result shown in Table 9. In contrast to what was found for the more complex GSM medium, the culture produced only intracellular lipase activity when grown in LM-1 medium. The hog lipase control showed lower enzyme activity than the bacterial enzyme when assayed at 50° C.

In an LM-3 medium, bacterial lipase production was scaled up to 6 liters using a New Brunswick 14-liter fermenter equipped with a funnel-shaped draft tube. Six liters of broth were harvested at 68 hours of growth and passed through a continuous centrifuge to collect approximately 160 milliliters of wet cells. A portion of the wet cells were treated with acetone to prepare a whole cell fractionator at 30,000 pounds per square inch gage prior to making the acetone powder. Lipase assays of these two preparations are compared in Table 10. The ruptured cell preparation contained twice as much lipase activity as the whole cell preparation, indicating that more intracellular enzyme was freed by the rupturing process. In LM-2 medium containing less phosphate and yeast extract, growth conditions were similar, but growth was terminated at 100 hours, and pH was not controlled. These results are also shown in Table 10.

Effect of temperature on two bacterial lipase preparations compared to control hog lipase is shown in FIG. 1. Hog lipase had optimum activity temperatures between 22° C and 40° C, while the two bacterial preparations displaced their highest activities at the highest temperatures tested.

Figure 2:
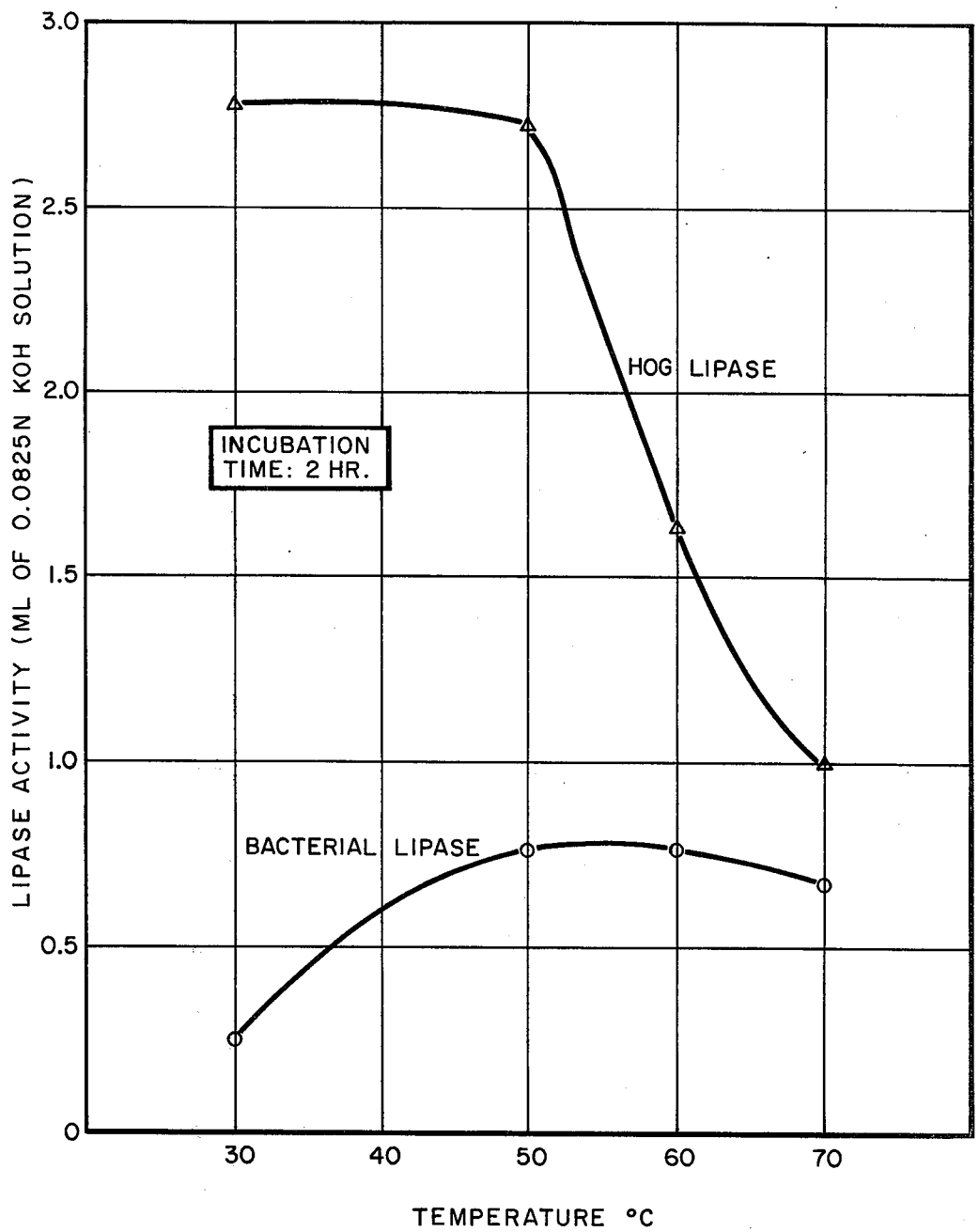

Bacterial intracellular lipase and the control hog lipase were tested for their thermal stability between 30° C and 70° C. The results are shown in FIG. 2. The bacterial enzyme had stability at 70° C, the highest temperature tested.

TABLE 9

BACTERIAL LIPASE ACTIVITES - LM-1 SHAKE FLASK GROWTH

| Lipase Inducer | Enzyme Preparation | LIPASE ACTIVITY AT 50° C Run 1 | Run 2 |
|---|---|---|---|
| n-Paraffin | Intracellular | 3.7 | 3.85 |
|  | Extracellular | 0.0 | — |
|  | Hog Lipase | — | 2.31 |

TABLE 10

INTRACELLULAR LIPASE PREPARED BY TWO DIFFERENT METHODS

| Medium | Preparation | Lipase Activity |
|---|---|---|
| LM-3 | Whole Cell Acetone Powder | 1.10 |
|  | Ruptured Cell Acetone Powder | 2.20 |
| LM-2 | Whole Cell Acetone Powder | 0.23 |
|  | Hog Lipase | 3.38 |

TABLE 10-continued

INTRACELLULAR LIPASE PREPARED BY TWO DIFFERENT METHODS

| Medium | Preparation | Lipase Activity |
|---|---|---|
|  | Hog Lipase Acetone Powder | 2.78 |

Figure 3:
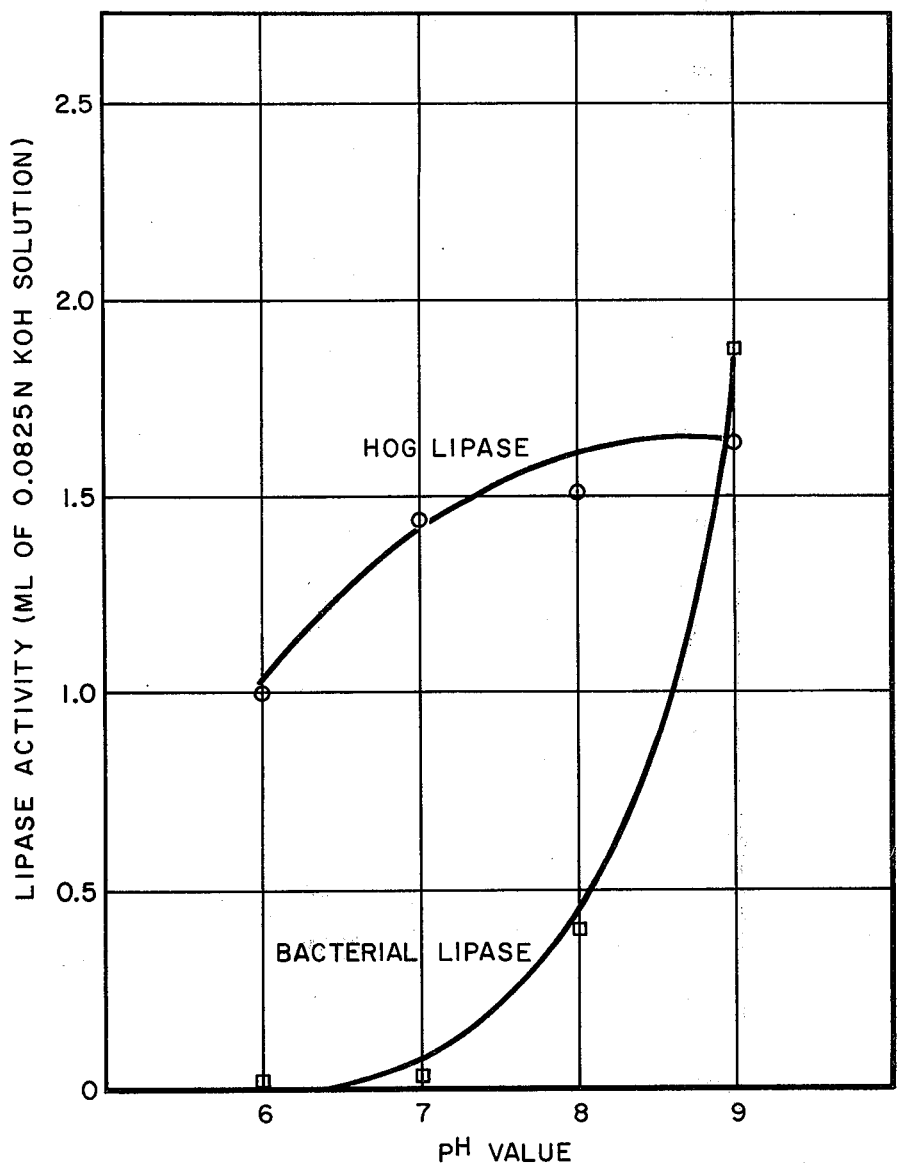

The effect of pH on intracellular bacterial lipase in a 0.1 molar tris-buffer system was tested, with the results shown in FIG. 3. Bacterial lipase showed relatively poor activity at pH 6 but very high activity at pH of 9. Control hog lipase also demonstrated optimal activity at pH 9.

An alkaline titration method was used for assaying lipase activity. For the alkaline titration method, duplicate 250-milliliter flasks were used, each containing 8 milliliters distilled water, 2 milliliters emulsified olive oil in polyvinyl alcohol, and 3 milliliters enzyme solution in M/15 phosphate buffer at a pH of 8.2. Commercial hog lipase was employed as an active lipase control. The mixture was well shaken and incubated statically at a specific temperature for a 2 -hour period. Thirty milliliters of ethanol and 15 milliliters of ether were added to stop the growth and to dissolve any hydrolyzed fatty acids present. The acids were then titrated with a standard 0.0825 N alcoholic potassium hydroxide solution using phenolphethalein as the indicator. Blank flask identical to test flasks had alcohol and ether added at zero time and were then titrated. Lipase activity was determined by subtracting the average blank value from the average experimental value. The lipase activity was expressed in milliliters of .0825 N potassium hydroxide consumed per 15 grams of enzymes for 2 hours. The alkaline titration method was used to evaluate lipase activity in a culture broth containing cells, and a 1 percent toluene was added to the reaction mixture to suppress cellular growth during the assay.

Bacterial cultures grown on $C^{12}$–$C^{14}$ n-paraffins and LM media produced not only intracellular lipase but also an extracellular pyocyanine pigment. The pigment production appeared to be influenced by medium composition. In four commercial peptone media containing 1 percent n-paraffins, the pigment yield, on the basis of a green color intensity test, showed a decreasing order for bacterial peptone which was greater than neopeptone which in turn was equal to protease peptone which in turn was greater than trypticase. The use of olive oil in place of the n-paraffin in the respective mediums showed that only the bacterial peptone medium allowed pigment formation, and then only at an extremely low level.

The pigment, in a cell-free broth, was extracted into chloroform for purification. The purified pyocyanine gave an infrared spectrum that closely resembled the one for standard pyocyanine compounds.

While certain embodiments and details have been shown for the purpose of illustrating this invention, it will be apparent to those skilled in this art that various changes and modifications may be made herein without departing from the spirit or the scope of the invention.

We claim:

1. A method for the bacterial production of Lipase from n-paraffin substrates comprising growing a Pseudomonas-like bacteria designated NRRL B-8110 on a substrate comprising n-paraffins having from 10 to 22 carbon atoms (b) allowing the bacterial cell growth to reach optimum levels; (c) separating the cells from the substrate; (d) rupturing the cell walls; (e) removing cell debris; and (f) recovering the lipase.

2. A method as described in claim 1 wherein the n-paraffins are selected from the group consisting of decane, undecane, dodecane, tetradecane, hexadecane, octadecane, nonedecane, eicosane, and docosane.

3. A method as described in claim 1 wherein the cell growth occurs at a temperature from 20° to 50° C.

4. A method as described in claim 1 wherein the cell growth is carried out for a period from 10 to 100 hours.

5. A method as described in claim 1 wherein the substrate is olive oil.

6. A method as described in claim 1 wherein the growth medium is selected from the group consisting of mineral salts, soybean dextrin and grease splitting.

* * * * *

UNITED STATES PATENT OFFICE
CERTIFICATE OF CORRECTION

PATENT NO. : 4,019,959
DATED : April 26, 1977
INVENTOR(S) : Len J. Gawel and Chi-Sin Chen It is certified that error appears in the above-identified patent and that said Letters Patent are hereby corrected as shown below:

Column 1, line 38, - delete "micororganisms" and insert --microorganisms--.

Column 1, line 39, - delete "product" and insert --produce--

Column 4, Table 6, under heading Alkane, - delete "$< C_{16}$" and insert --$> C_{16}$--.

Column 4, Table 7, - delete "Lipase Activites ..." and insert --Lipase Activities...--.

Column 6, line 27, - delete "phenolphethalein" and insert --phenolphthalein--.

Column 6, line 28, - delete "flask" and insert --flasks--.

Column 6, Claim 1, line 2, - insert (a) before the word growing.

Signed and Sealed this nineteenth Day of July 1977

[SEAL]

Attest:

RUTH C. MASON
Attesting Officer

C. MARSHALL DANN
Commissioner of Patents and Trademarks